US009233935B2

(12) United States Patent
Reddy et al.

(10) Patent No.: US 9,233,935 B2
(45) Date of Patent: Jan. 12, 2016

(54) RILPIVIRINE HYDROCHLORIDE

(75) Inventors: Bandi Parthasaradhi Reddy, Hyderabad (IN); Kura Rathnakar Reddy, Hyderabad (IN); Dasari Muralidhara Reddy, Hyderabad (IN); Adulla Venkat Narsimha Reddy, Hyderabad (IN); Bandi Vamsi Krishna, Hyderabad (IN)

(73) Assignee: HETERO RESEARCH FOUNDATION (IN)

(*) Notice: Subject to any disclaimer, the term of this patent is extended or adjusted under 35 U.S.C. 154(b) by 0 days.

(21) Appl. No.: 14/344,791

(22) PCT Filed: Sep. 10, 2012

(86) PCT No.: PCT/IN2012/000600
§ 371 (c)(1),
(2), (4) Date: Mar. 13, 2014

(87) PCT Pub. No.: WO2013/038425
PCT Pub. Date: Mar. 21, 2013

(65) Prior Publication Data
US 2014/0350038 A1 Nov. 27, 2014

(30) Foreign Application Priority Data
Sep. 16, 2011 (IN) .......................... 3191/CHE/2011

(51) Int. Cl.
*C07D 239/48* (2006.01)
*A61K 31/505* (2006.01)

(52) U.S. Cl.
CPC .............. *C07D 239/48* (2013.01); *A61K 31/505* (2013.01)

(58) Field of Classification Search
CPC ........................ C07D 239/48; C07D 1531/505
See application file for complete search history.

(56) References Cited

U.S. PATENT DOCUMENTS

| | | | |
|---|---|---|---|
| 5,492,915 A | 2/1996 | Dereu et al. | |
| 7,125,879 B2 | 10/2006 | Guillemont et al. | |
| 7,399,856 B2 | 7/2008 | Schils et al. | |
| 7,563,922 B2 | 7/2009 | Schils et al. | |
| 7,705,148 B2 | 4/2010 | Schils et al. | |
| 7,956,063 B2 | 6/2011 | Guillemont et al. | |
| 2003/0186990 A1 | 10/2003 | Kukla et al. | |
| 2005/0197354 A1 | 9/2005 | Andries et al. | |
| 2014/0228385 A1* | 8/2014 | Reddy et al. ................. | 514/275 |

FOREIGN PATENT DOCUMENTS

| | | | |
|---|---|---|---|
| IN | 2010CH03871 | * | 2/2014 |
| WO | WO 03016306 A1 | * | 2/2003 |
| WO | WO 2004016581 A1 | * | 2/2004 |
| WO | WO 2004050068 A1 | * | 6/2004 |
| WO | WO 2005021001 A1 | * | 3/2005 |
| WO | WO 2006024668 A1 | * | 3/2006 |
| WO | WO 2012143937 A2 | * | 10/2012 |
| WO | WO 2012147091 A2 | * | 11/2012 |

OTHER PUBLICATIONS

D. Schils et al., 12 Organic Process Research & Development, 530-536 (2008).*
M. Pendela et al., 49 Journal of Pharmaceutical and Biomedical Analysis, 508-512 (2009).*
J. Guillemont, 48 Journal of Medicinal Chemistry, 2072-2079 (2005).*
Polymorphism in Pharmaceutical Solids (H.G. Brittain ed., 2nd ed., 2009).*
Preformulation in Solid Dosage Form Development (M. C. Adeyeye et al., eds., 2008).*
Solid State Characterization of Pharmaceuticals 473-491 (R.A. Storey et al., eds., 2011).*
International Search Report; International Application No. PCT/IN2012/000600; International Filing Date Oct. 9, 2012; 1 page.

* cited by examiner

*Primary Examiner* — Alexander R Pagano
(74) *Attorney, Agent, or Firm* — Cantor Colburn LLP

(57) ABSTRACT

The present invention provides a novel process for the preparation of rilpivirine. The present invention also provides a novel process for the preparation of rilpivirine hydrochloride. The present invention further provides a rilpivirine hydrochloride monohydrate, process for its preparation and pharmaceutical compositions comprising it.

10 Claims, No Drawings

RILPIVIRINE HYDROCHLORIDE

CROSS-REFERENCE TO RELATED APPLICATIONS

This application is a U.S. national stage of international application No. PCT/IN2012/000600, filed on Sep. 10, 2012, the disclosure of which is incorporated herein by reference in its entirety. This application claims the benefit of Indian Provisional patent Application No. 3191/CHE/2011, filed on Sep. 16, 2011, which is incorporated herein by reference in its entirety.

FIELD OF THE INVENTION

The present invention provides a novel process for the preparation of rilpivirine. The present invention also provides a novel process for the preparation of rilpivirine hydrochloride. The present invention further provides a rilpivirine hydrochloride monohydrate, process for its preparation and pharmaceutical compositions comprising it.

BACKGROUND OF THE INVENTION

Rilpivirine, chemically 4-[[4-[[4-(2-cyanoethenyl)-2,6-dimethylphenyl]amino]pyrimidinyl]amino]benzonitrile and has the structural formula:

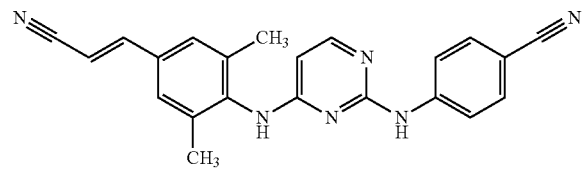 [SMILES: Cc1cc(/C=C/C#N)cc(C)c1Nc1ccnc(Nc2ccc(C#N)cc2)n1]

Rilpivirine (TMC278) is an investigational new drug, developed by Tibotec, for the treatment of HIV infection. It is a second-generation non-nucleoside reverse transcriptase inhibitor (NNRTI) with higher potency, longer half-life and reduced side-effect profile compared with older NNRTIs.

Polymorphism is defined as "the ability of a substance to exist as two or more crystalline phases that have different arrangement and/or conformations of the molecules in the crystal Lattice. Thus, in the strict sense, polymorphs are different crystalline structures of the same pure substance in which the molecules have different arrangements and/or different configurations of the molecules". Different polymorphs may differ in their physical properties such as melting point, solubility, X-ray diffraction patterns, etc. Although those differences disappear once the compound is dissolved, they can appreciably influence pharmaceutically relevant properties of the solid form, such as handling properties, dissolution rate and stability. Such properties can significantly influence the processing, shelf life, and commercial acceptance of a polymorph. It is therefore important to investigate all solid forms of a drug, including all polymorphic forms, and to determine the stability, dissolution and flow properties of each polymorphic form. Polymorphic forms of a compound can be distinguished in the laboratory by analytical methods such as X-ray diffraction (XRD), Differential Scanning Calorimetry (DSC) and Infrared spectrometry (IR).

Solvent medium and mode of crystallization play very important role in obtaining one polymorphic Form over the other.

Rilpivirine and its salts can exist in different polymorphic Forms, which may differ from each other in terms of stability, physical properties, spectral data and methods of preparation.

Rilpivirine and its hydrochloride salt were disclosed in U.S. Pat. No. 7,125,879.

Process for the preparation of rilpivirine was disclosed in U.S. Pat. No. 7,399,856 ('856 patent). According to the '856 patent, rilpivirine can be prepared by reacting the (E)-3-(4-amino-3,5-dimethylphenyl)acrylonitrile hydrochloride of formula II with 4-(4-chloropyrimidin-2-ylamino)benzonitrile of formula III-a in the presence of potassium carbonate and acetonitrile under reflux for 69 hours. The synthetic procedure is illustrated in scheme I, below:

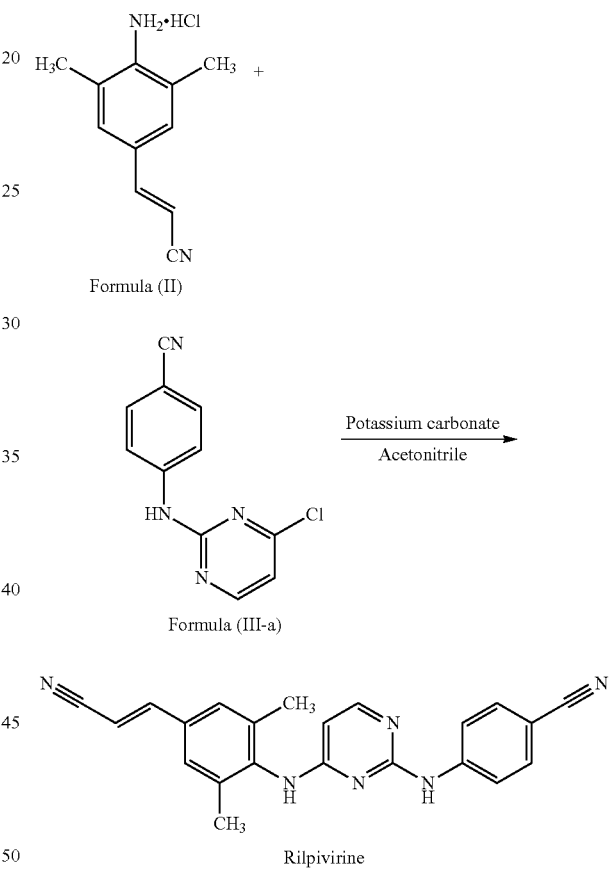

Process for the preparation of rilpivirine was disclosed in U.S. Pat. No. 7,705,148 ('148 patent). According to the '148 patent, rilpivirine can be prepared by reacting the 4-[[4-[[4-bromo-2,6-dimethylphenyl]amino]-2-pyrimidinyl]amino] benzonitrile with acrylonitrile in the presence of palladium acetate, N,N-diethylethanamine and tris(2-methylphenyl) phosphine in acetonitrile.

According to the '148 patent, rilpivirine can be prepared by reacting the compound of formula IV with 4-(4-chloropyrimidin-2-ylamino)benzonitrile formula III-a in the presence of hydrochloric acid and n-propanol to obtain a compound of formula VII, and then the compound was treated with acetonitrile and potassium carbonate under reflux for 69 hours. The synthetic procedure is illustrated in scheme II, below:

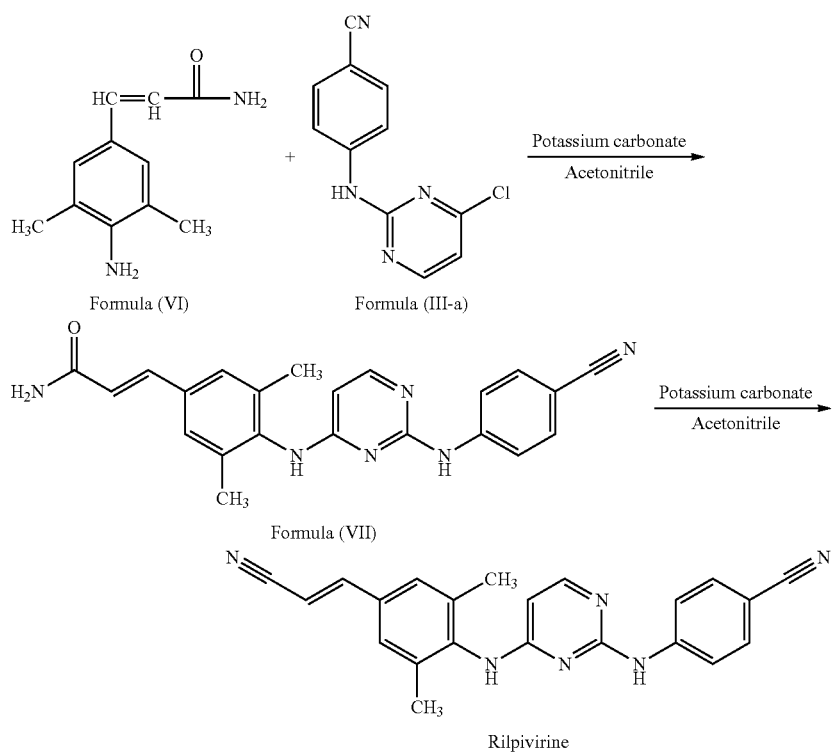

Scheme II

Rilpivirine

U.S. Pat. No. 7,563,922 disclosed a process for the preparation of (E)-3-(4-amino-3,5-dimethylphenyl)acrylonitrile hydrochloride. According to the patent, (E)-3-(4-amino-3,5-dimethylphenyl)acrylonitrile hydrochloride can be prepared by reacting the 4-iodo-2,6-dimethyl-benzenamine in N,N-dimethylacetamide with acrylonitrile in the presence of sodium acetate and toluene, and then the solid thus obtained was reacted with hydrochloric acid in 2-propanol in the presence of ethanol and diisopropyl ether.

U.S. Pat. No. 7,956,063 described a polymorphic Form A, Form B, Form C and Form D of rilpivirine hydrochloride.

An unpublished application, IN 1415/CHE/2011 assigned to Hetero Research Foundation discloses a process for the preparation of rilpivirine. According to the application, rilpivirine can be prepared by reacting the 4-(4-chloropyrimidin-2-ylamino)benzonitrile with (E)-3-(4-amino-3,5-dimethylphenyl)acrylonitrile hydrochloride in the presence of p-toluene sulfonic acid monohydrate and 1,4-dioxane.

It has been found that the rilpivirine produced according to the prior art procedures results in low yields. According to the present invention rilpivirine can be obtained in higher yields than the prior art processes.

We have found that a novel process for the preparation of rilpivirine. The process of the invention ensures that rilpivirine is obtained at faster rate with higher yields.

We have also found that a novel process for the preparation of rilpivirine hydrochloride.

The processes of present invention are simple, eco-friendly, inexpensive, reproducible, robust and is well suited on an industrial scale.

We have also found that a rilpivirine hydrochloride monohydrate.

Thus, one object of the present invention is to provide a novel process for the preparation of rilpivirine.

Another object of the present invention is to provide a novel process for the preparation of rilpivirine hydrochloride.

Another object of the present invention is to provide a rilpivirine hydrochloride monohydrate, process for its preparation and pharmaceutical compositions comprising it.

SUMMARY OF THE INVENTION

In one aspect, the present invention provides a novel process for the preparation of rilpivirine, which comprises:
a) condensing the (E)-3-(4-amino-3,5-dimethylphenyl) acrylonitrile hydrochloride with 4-(4-chloropyrimidin-2-ylamino)benzonitrile in the presence of N-methylpyrrolidone;
b) heating the contents obtained in step (a) at about 75 to 95° C. to obtain a solution;
c) cooling the solution obtained in step (b) at below 35° C.;
d) adding water to the reaction mass; and
e) isolating rilpivirine.

In another aspect, the present invention provides a novel process for the preparation of rilpivirine hydrochloride, which comprises:
a) suspending rilpivirine in an alcoholic solvent;
b) heating the contents obtained in step (a) at reflux;
c) adding a solution of hydrochloric acid in an alcoholic solvent to the reaction mixture at reflux;
d) maintaining the reaction mass at reflux; and
e) isolating pure rilpivirine hydrochloride.

In another aspect, the present invention provides a rilpivirine hydrochloride monohydrate.

In another aspect, the present invention provides a process for the preparation of rilpivirine hydrochloride monohydrate, which comprises:

a) suspending rilpivirine in an alcoholic solvent, a ketonic solvent or a mixture thereof;
b) heating the contents obtained in step (a) at reflux to obtain a solution;
c) adding carbon to the solution;
d) removing the solvent from the solution;
e) adding an alcoholic solvent to the residual solid obtained in step (d);
f) passing the hydrochloride gas to the reaction mass; and
g) isolating rilpivirine hydrochloride monohydrate.

Yet in another aspect, the present invention provides a pharmaceutical composition comprising rilpivirine hydrochloride monohydrate and pharmaceutically acceptable excipients.

DETAILED DESCRIPTION OF THE INVENTION

As used herein the term "room temperature" refers to a temperature of about 25° C. to about 35° C.

According to one aspect of the present invention, there is provided a novel process for the preparation of rilpivirine, which comprises:
a) condensing the (E)-3-(4-amino-3,5-dimethylphenyl) acrylonitrile hydrochloride with 4-(4-chloropyrimidin-2-ylamino)benzonitrile in the presence of N-methylpyrrolidone;
b) heating the contents obtained in step (a) at about 75 to 95° C. to obtain a solution;
c) cooling the solution obtained in step (b) at below 35° C.;
d) adding water to the reaction mass; and
e) isolating rilpivirine.

The reaction in step (b) may preferably be heated to 100 to 110° C.

Step (c) may preferably be carried out at room temperature.

Rilpivirine may be isolated in step (e) by the methods known such as filtration or centrifugation.

According to another aspect of the present invention, there is provided a novel process for the preparation of rilpivirine hydrochloride, which comprises:
a) suspending rilpivirine in an alcoholic solvent;
b) heating the contents obtained in step (a) at reflux;
c) adding a solution of hydrochloric acid in an alcoholic solvent to the reaction mixture at reflux;
d) maintaining the reaction mass at reflux; and
e) isolating pure rilpivirine hydrochloride.

The alcoholic solvent used in step (a) and step (c) may preferably be a solvent or mixture of solvents selected from methanol, ethanol, isopropanol, tert-butyl alcohol, n-butanol and isobutyl alcohol, and more preferably the alcoholic solvents are methanol and isopropanol.

Isolation of rilpivirine hydrochloride in step (e) can be performed by conventional methods such as cooling, removal of solvents, concentrating the reaction mass, adding an antisolvent, extraction with a solvent and the like.

According to another aspect of the present invention, there is provided a rilpivirine hydrochloride monohydrate.

Rilpivirine hydrochloride monohydrate may contain water content. The water content of the rilpivirine hydrochloride monohydrate may be in between 3.0 to 6.0% by weight and typically may be in between 3.5 to 5.5% by weight.

According to another aspect of the present invention, there is provided a process for the preparation of rilpivirine hydrochloride monohydrate, which comprises:
a) suspending rilpivirine in an alcoholic solvent, a ketonic solvent or a mixture thereof;
b) heating the contents obtained in step (a) at reflux to obtain a solution;
c) adding carbon to the solution;
d) removing the solvent from the solution;
e) adding an alcoholic solvent to the residual solid obtained in step (d);
f) passing the hydrochloride gas to the reaction mass; and
g) isolating rilpivirine hydrochloride monohydrate.

The alcoholic solvent used in step (a) and step (e) may preferably be a solvent or mixture of solvents selected from methanol, ethanol, isopropanol, tert-butyl alcohol, n-butanol and isobutyl alcohol, and more preferably the alcoholic solvent is methanol.

Preferably the ketonic solvent used in step (a) may be a solvent or mixture of solvents selected from acetone, methyl ethyl ketone, methyl isobutyl ketone and diethyl ketone. More preferably the ketonic solvent is acetone.

Removal of the solvent in step (d) may be carried out at atmospheric pressure or at reduced pressure. Removal of the solvent may preferably be carried out until the solvent is almost completely distilled off.

Rilpivirine hydrochloride monohydrate may be isolated in step (g) by the methods known such as filtration or centrifugation.

According to another aspect of the present invention, there is provided a pharmaceutical composition comprising rilpivirine hydrochloride monohydrate and pharmaceutically acceptable excipients, and optionally other therapeutic ingredients. The rilpivirine hydrochloride monohydrate may preferably be formulated into tablets, capsules, suspensions, dispersions, injectables or other pharmaceutical forms.

The contents of rilpivirine, rilpivirine hydrochloride, rilpivirine hydrochloride monohydrate and the impurities are determined by High performance liquid chromatography (HPLC).

The invention will now be further described by the following examples, which are illustrative rather than limiting.

PREPARATIVE EXAMPLES

Preparative Example 1

Preparation of 4-(4-chloropyrimidin-2-ylamino)benzonitrile

Step-I: Preparation of 2,4-dichloro pyrimidine

To a mixture of N,N-dimethyl aniline (140 gm) and uracil (100 gm) was added phosphorous oxychloride (342 gm) slowly at 0° C. The contents were then heated to reflux and maintained for 4 hours. The solution was then cooled to room temperature, then transferred into ice water and stirred for 1 hour. The resulting precipitate was filtered and washed with water. The solid thus obtained was recrystallized from hexane to give 80 gm of 2,4-dichloro pyrimidine.

Step-II: Preparation of 2-chloro-4-methoxypyrimidine

To a solution of 2,4-dichloro pyrimidine (20 gm) in methanol (200 ml) was added sodium methoxide (8.7 gm) at 0 to 5° C. The resulting mixture was stirred for 14 hours at room temperature and then concentrated under reduced pressure to obtain a residual mass. The residual mass obtained was extracted with ethyl acetate and water. The combined organic layers were washed with water and sodium chloride solution, and then concentrated under vacuum to obtain a crude solid. The crude solid obtained was dissolved in hexane (40 ml) at 0 to 5° C. and stirred for 1 hour. The solid obtained was collected by filtration and then dried to obtain 9.7 gm of 2-chloro-4-methoxypyrimidine.

Step-III: Preparation of 4-(4-methoxypyrimidin-2-ylamino) benzonitrile 1,4-Dioxane (100 ml) was added to a mixture of 2-chloro-4-methoxypyrimidine (20 gm), 4-aminobenzonitrile (16.33 gm) and p-toluene sulfonic acid (42.12 gm). The mixture was then heated to 100 to 110° C. and stirred for 14 hours. The solution was then cooled to room temperature and basified with saturated sodium bicarbonate solution. The layers were separated and the aqueous layer was extracted with ethyl acetate. The combined organic layers were washed with water and then concentrated to obtain a residual solid. The residual solid obtained was slurried in isopropyl alcohol at room temperature for 30 minutes and filtered. The solid obtained was then dried to give 17.3 gm of 4-(4-methoxypyrimidin-2-ylamino)benzonitrile.

Step-IV: Preparation of 4-(4-hydroxypyrimidin-2-ylamino) benzonitrile

Pyridine hydrochloride (23 gm) was added to 4-(4-methoxypyrimidin-2-ylamino)benzonitrile (15 gm) and then heated to 150 to 160° C. for 3 hours. The mixture was then cooled to room temperature, then transferred into ice water and stirred for 1 hour. The resulting precipitate was filtered and washed with water. The solid thus obtained was slurried in acetonitrile at 0 to 5° C. for 1 hour and filtered. The solid obtained was dried to give 12.3 gm of 4-(4-hydroxypyrimidin-2-ylamino)benzonitrile.

Step-V: Preparation of 4-(4-chloropyrimidin-2-ylamino)benzonitrile

Phosphorous oxychloride (104 gm) was added slowly to 4-(4-hydroxypyrimidin-2-ylamino)benzonitrile (12 gm) at 0° C. and then heated to reflux for 1 hour. The solution was then cooled to room temperature, stirred for 30 minutes and filtered. The precipitated solid thus obtained was dissolved in isopropyl alcohol at 0 to 5° C. and stirred for 1 hour at 0 to 5° C. The solid obtained was collected by filtration and then dried to obtain 9.75 gm of 4-(4-chloropyrimidin-2-ylamino) benzonitrile.

Preparative Example 2

Preparation of (E)-3-(4-amino-3,5-dimethylphenyl)acrylonitrile hydrochloride

Step-I: Preparation of 4-iodo-2,6-dimethyl benzenamine

To a solution of 2,6-dimethyl aniline (50 gm) in 1,4-dioxane (400 ml) and pyridine (40 ml) was added iodine (157.3 gm) slowly at 0° C. The solution was stirred for 1 hour at 0° C. and the temperature was raised to room temperature. The solution was stirred for 1 hour at room temperature and then added a saturated solution of sodium thiosulfate. The layers were separated and the aqueous layer was extracted with methylene chloride. The combined organic layers were dried with anhydrous sodium sulfate and the solvent was evaporated in vacuum to obtain 91.8 gm of 4-iodo-2,6-dimethyl benzenamine.

Step-II: Preparation of (E)-3-(4-amino-3,5-dimethylphenyl)acrylonitrile hydrochloride Sodium acetate (13.27 gm), palladium on charcoal (0.858 gm) and dimethylacetamide (400 ml) were added and then heated to 140° C. under nitrogen atmosphere. A solution of 4-iodo-2,6-dimethyl benzenamine (20 gm), acrylonitrile (10.72 ml) and dimethylacetamide (200 ml) was added slowly to the reaction mixture. The reaction mixture was maintained for 12 hours at 140° C. The reaction mass was then cooled to room temperature and filtered through celite. The filtrate obtained was treated with water and then the layers were separated. The aqueous layer was extracted with ethyl acetate and the combined organic layers were washed with water and sodium chloride solution. The organic layer was dried with sodium sulfate and the solvent was evaporated in vacuum to obtain crude oily residue.

To the crude oily residue obtained above was added ethanol (210 ml). The solution was then heated to 60° C. and then added a solution of hydrochloride in isopropyl alcohol (69.5 ml). The reaction mixture was stirred for 1 hour at 60° C. and then cooled to room temperature. The solid obtained was collected by filtration and then dried to obtain 11.5 gm of (E)-3-(4-amino-3,5-dimethylphenyl)acrylonitrile hydrochloride.

EXAMPLES

Example 1

Preparation of rilpivirine

To a mixture of 4-(4-chloropyrimidin-2-ylamino)benzonitrile (85 gm) as obtained in preparative example 1 and (E)-3-(4-amino-3,5-dimethylphenyl)acrylonitrile hydrochloride (69 gm) as obtained in preparative example 2 was added N-methylpyrrolidone (425 ml) under stirring. The mixture was then heated to 85 to 95° C. and stirred for 16 hours. The solution was then cooled to room temperature and then added water (1105 ml). The reaction mass was stirred for 1 hour 30 minutes at room temperature and filtered. The solid obtained was then dried to obtain 135 gm of rilpivirine as a white solid.
Chromatographic purity of rilpivirine: 98.6%;
Content of Z-isomer: 1.2%.

Example 2

Preparation of rilpivirine hydrochloride

Rilpivirine (135 gm) as obtained in example 1 was suspended in methanol (1350 ml) and then heated to reflux for 20 minutes. To the reaction mixture was added a solution of hydrochloric acid in isopropanol (6N, 675 ml) at reflux and maintained for 1 hour. The reaction mass was then cooled to room temperature and stirred for 1 hour at room temperature. The solid obtained was collected by filtration and then dried to obtain 86 gm of rilpivirine hydrochloride.
Chromatographic purity of rilpivirine hydrochloride: 99.9%;
Content of Z-isomer: 0.08%.

Example 3

Preparation of rilpivirine hydrochloride monohydrate

Rilpivirine (100 gm) was suspended in a mixture of methanol (1500 ml) and acetone (2200 ml). The contents were heated to reflux and maintained for 30 minutes at reflux to obtain a clear solution. The solution was treated with carbon and stirred for 10 minutes. The reaction mass was filtered through celite bed and then concentrated to obtain a residual solid. The residual solid was stirred for 30 minutes, filtered and then dried. To the solid thus obtained was added methanol and then the reaction mass was passed dry hydrochloride gas until the precipitation obtained at 0° C. The temperature of the reaction mass was raised to room temperature and stirred for 1 hour at room temperature. The separated solid was filtered and then dried to obtain 87.5 gm of rilpivirine hydrochloride crystalline monohydrate as an off white solid.

Chromatographic purity of rilpivirine hydrochloride monohydrate: 99.93%;
Content of Z-isomer: 0.05%.

Example 4

Preparation of rilpivirine hydrochloride monohydrate

Example 3 was repeated using ethanol solvent instead of methanol solvent to obtain rilpivirine hydrochloride monohydrate.

Example 5

Preparation of rilpivirine hydrochloride monohydrate

Example 3 was repeated using isopropanol solvent instead of methanol solvent to obtain rilpivirine hydrochloride monohydrate.

Example 6

Preparation of rilpivirine hydrochloride monohydrate

Example 3 was repeated using methyl ethyl ketone solvent instead of acetone solvent to obtain rilpivirine hydrochloride monohydrate.

We claim:

1. Crystalline rilpivirine hydrochloride monohydrate having the structure

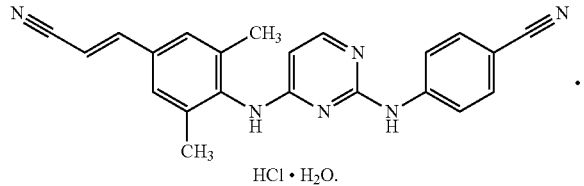

$HCl \cdot H_2O$.

2. The crystalline rilpivirine hydrochloride monohydrate as claimed in claim 1, further comprising 0.05% to 1.2% Z-isomer of 4-[[4-[[4-(2-cyanoethenyl)-2,6-dimethylphenyl]amino]pyrimidinyl]amino]benzonitrile.

3. A pharmaceutical composition comprising the crystalline rilpivirine hydrochloride monohydrate of claim 1 and pharmaceutically acceptable excipients.

4. The pharmaceutical composition as claimed in claim 3, wherein the crystalline rilpivirine hydrochloride monohydrate is formulated into tablets, capsules, suspensions, dispersions or injectables.

5. The pharmaceutical composition as claimed in claim 3, wherein the crystalline rilpivirine hydrochloride monohydrate, further comprises 0.05% to 1.2% Z-isomer of 4-[[4-[[4-(2-cyanoethenyl)-2,6-dimethylphenyl]amino]pyrimidinyl]amino]benzonitrile.

6. A process for the preparation of crystalline rilpivirine hydrochloride monohydrate, which comprises:
   a. suspending rilpivirine in an alcoholic solvent, a ketonic solvent or a mixture thereof;
   b. heating the contents obtained in step (a) at reflux to obtain a solution;
   c. adding carbon to the solution;
   d. removing the solvent from the solution;
   e. adding an alcoholic solvent to the residual solid obtained in step (d);
   f. passing the hydrochloride gas to the reaction mass; and
   g. isolating crystalline rilpivirine hydrochloride monohydrate.

7. The process as claimed in claim 6, wherein the alcoholic solvent used in step (a) and step (e) is a solvent or mixture of solvents selected from methanol, ethanol, isopropanol, tert-butyl alcohol, n-butanol and isobutyl alcohol.

8. The process as claimed in claim 7, wherein the alcoholic solvent is methanol.

9. The process as claimed in claim 6, wherein the ketonic solvent used in step (a) is a solvent or mixture of solvents selected from acetone, methyl ethyl ketone, methyl isobutyl ketone and diethyl ketone.

10. The process as claimed in claim 9, wherein the ketonic solvent is acetone.

* * * * *